United States Patent [19]

Akashi et al.

[11] 4,346,169

[45] Aug. 24, 1982

[54] METHOD FOR PRODUCTION OF L-ARGININE BY FERMENTATION

[75] Inventors: Kunihiko Akashi, Saga; Yayoi Nakamura, Ayase; Takayasu Tsuchida, Kawasaki; Hiroe Yoshii; Shigeho Ikeda, both of Yokohama, all of Japan

[73] Assignee: Ajinomoto Company, Incorporated, Tokyo, Japan

[21] Appl. No.: 187,146

[22] Filed: Sep. 15, 1980

[51] Int. Cl.$^3$ .............................................. C12P 13/10
[52] U.S. Cl. ................................... 435/114; 435/840; 435/843; 435/172
[58] Field of Search ............................... 435/114, 172

[56] References Cited

FOREIGN PATENT DOCUMENTS 52-38088  3/1977  Japan .................................... 435/110

OTHER PUBLICATIONS

Kubota et al., in Journal General Applied Microbiology, vol. 19, pp. 339–352 (1973).
Tosaka et al., in Chemical Abstracts, vol. 91:156040c, 1979 (Japan Kokai 79 89,085, Jul. 14, 1979).

*Primary Examiner*—Lionel M. Shapiro
*Attorney, Agent, or Firm*—Oblon, Fisher, Spivak, McClelland & Maier

[57] ABSTRACT

Mutants of the genus Bervibacterium or Corynebacterium are given resistance to keto-malonic acid, fluoro-malonic acid, monofluoro-acetic acid or aspartate antagonist and used to produce L-arginine by aerobic fermentation.

5 Claims, No Drawings

METHOD FOR PRODUCTION OF L-ARGININE BY FERMENTATION

BACKGROUND OF THE INVENTION

This invention relates to a method for producing L-arginine by fermentation.

It has been known that L-arginine is produced by a fermentation process, in which mutants of the genus Brevibacterium, Coryne-bacterium resistant to a sulfa drug or arginine antagonist are used (Japanese Published Unexamined Patent Application No. 48189/1975).

SUMMARY OF THE INVENTION

It has now been found that the productivity of L-arginine is significantly increased when a resistance to keto-malonic acid, fluoro-malonic acid, monofluoro acetic acid, or aspartate-antagonist is given to the known mutants which belong to the genus Brevibacterium or Corynebacterium and are capable of producing a L-arginine.

DETAILED DESCRIPTION OF THE PREFERRED EMBODIMENTS

The microorganisms employed according to the present invention are the mutants which belong to the genus Brevibacterium or Corynebacterium, are resistant to keto-malonic acid, fluoro-malonic acid, monofluoroacetic acid or aspartate-antagonists and have the ability to produce L-arginine.

The mutants as stated above may be induced from parents strains of the genus Brevibacterium or Corynebacterium by conventional mutation methods such as an irradiation with UV-ray or exposure to N-methyl-N'-nitro-N-nitroso guanidine, and thereafter picking up the colonies which are formed on the nutrient agar-medium containing the amount of the chemical agents inhibitive to the growth of the parent strain.

As the parent strains, mutants capable of producing L-arginine or wild strains of the genus Brevibacterium or Corynebacterium are employed. When the wild strains are used as the parent, L-arginine productivity is given to the wild strains prior to giving the resistance to the chemicals of this invention, or after giving to the wild strains the resistance, L-arginine productivity is given.

In order to give the L-arginine productivity to the microorganisms of the genus Brevibacterium or Corynebacterium, as is known, resistance to arginine-antagonists such as 2-thiazole alanine and arginine hydroxamate, or to sulfa-drug is given to the microorganisms. The arginine antagonists are such chemicals as those which inhibit the growth of the microorganisms of the genus Brevibacterium and Corynebacterium and the inhibition is suppressed when L-arginine coexists in the medium.

The preferred wild strains belonging to the genus Brevibacterium or Corynebacterium and are coryneform L-glutamic acid producing bacteria and the examples are:

| | |
|---|---|
| Brevibacterium divaricatum | ATCC 14020, |
| Brevibacterium flavum | ATCC 14067, |
| Brevibacterium lactofermentum | ATCC 13869, |
| Brevibacterium saccharolyticum | ATCC 14066, |
| Brevibacterium roseum | ATCC 13825, |
| Corynebacterium acetoacidophilum | ATCC 13870, |
| Corynebacterium lilium | ATTC 15990, and |
| Corynebacterium glutamicum | ATCC 13032. |

Aspartate-antagonists of this invention inhibit the growth of the microorganisms of genus Brevibacterium and Corynebacterium and the inhibition is suppressed partly or completely when L-aspartate coexists in the medium, and are, for instance, $\beta$-aspartylhydrazide, diamino-succinic acid and hadacidin.

Specimens of the mutants of this invention are:

| | |
|---|---|
| Brevibacterium flavum | AJ 11337, FERM-P 4940, NRRL B-12235 (SD$^\gamma$, AspHd$^\gamma$) |
| Brevibacterium flavum | AJ 11338, FERM-P 4941, NRRL B-12236 (SD$^\gamma$, AS$^\gamma$) |
| Brevibacterium flavum | AJ 11339, FERM-P 4942, NRRL B-12237 (SD$^\gamma$, HD$^\gamma$) |
| Corynebacterium acetoacidophilum | AJ 11341, FERM-P 4944, NRRL B-12238 (SD$^\gamma$, AspHd$^\gamma$) |
| Corynebacterium acetoacidophilum | AJ 11342, FERM-P 4945, NRRL B-12239 (SD$^\gamma$, AS$^\gamma$) |
| Brevibacterium flavum | AJ 11343, FERM-P 4946, NRRL B-12240 (2TA$^\gamma$, SG$^\gamma$, His$^-$, HD$^\gamma$) |
| Brevibacterium flavum | AJ 11595, FERM-P 5637, NRRL B-12242 (SD$^\gamma$, KM$^\gamma$) |
| Brevibacterium flavum | AJ 11596, FERM-P 5638, NRRL B-12243 (SD$^\gamma$, FM$^\gamma$) |
| Brevibacterium flavum | AJ 11597, FERM-P 5639, NRRL B-12244 (SD$^\gamma$, FA$^\gamma$) |
| Corynebacterium acetoacidophilum | AJ 11598, FERM-P 5640, NRRL B-12245 (SD$^\gamma$, KM$^\gamma$) |
| Brevibacterium flavum | AJ 11344, FERM-P 4947, NRRL B-12241 (2TA$^\gamma$, SG$^\gamma$, His$^-$, HD$^\gamma$) |
| Corynebacterium acetoacidophilum | AJ 11599, FERM-P 5641, NRRL B-12246 (SD$^\gamma$, FA$^\gamma$) |
| Brevibacterium flavum | AJ 11600, FERM-P 5642, NRRL B-12247 (2TA$^\gamma$, SG$^\gamma$, His$^-$, FA$^\gamma$) |

SD$^\gamma$: resistance to sulfadiazine
2TA$^\gamma$: resistance to 2-thiazolealanine
SG$^\gamma$: resistance to sulfaguanidine
His$^-$: requirement of histidine for growth
Asp Hd$^\gamma$: resistance to aspartylhydrazide
AS$^\gamma$: resistance to diaminosuccinic acid
HD$^\gamma$: resistance to hadacidin
KM$^\gamma$: resistance to keto-malonic acid
FM$^\gamma$: resistance to fluoro-malonic acid
FA$^\gamma$: resistance to monofluoro-acetic acid The method by which the mutants of the present invention were induced are shown below:

Experiment 1

Brevibacterium flavum AJ 3277 (SD$^\gamma$) which was derived from ATCC 14067 was treated with 250 $\mu$g/ml N-methyl-N'-nitro-N-nitro-soguanidine at 30° C. for 30 minutes. Then, the microbial cells were spread on an agar medium containing the amount of keto-malonic acid which inhibit the growth of the parent strain.

After the cultivation, colonies which turned up on the agar medium were picked up and their productivities of L-arginine were examined.

Among the mutants thus obtained, B. flavum AJ 11595 which can produce more increased amount of L-arginine than any other mutants was selected.

The other mutants of this invention were obtained by the analogous manner. The degree of the resistance of the mutants of this invention to the chemical agents were determined by the following experiment.

Experiment 2

Each testing strain was washed with the aqueous culture medium shown in Table 1, the cells were suspended in the same medium (the optical density at 562 mm of 26 times dilute of the suspension was 0.3 to 0.33), and 0.1 ml of the suspension was put into 40 ml of the same medium which further contains the amount of chemical agents shown in Table 2 and 3 and was placed in a small-size test tube.

TABLE 1

| Composition of agar-medium (pH: 7.2) | | | |
|---|---|---|---|
| Component | Conc. | Component | Conc. |
| Glucose | 2.0 g/dl | $FeSO_4.7H_2O$ | 10 mg/dl |
| Urea | 0.3 g/dl | $MnSO_4.4H_2O$ | 1.0 mg/dl |
| Ammonium sulfate | 1.0 g/dl | Biotin | 10 mg/dl |
| $KH_2PO_4$ | 0.1 g/dl | Thiamine.HCl | 100 μg/l |
| $MgSO_4.7H_2O$ | 0.04 g/dl | | |

A cultivation was carried out at 31.5° C. for 48 hours with shaking. Then, the growth of each strain was determined by measuring the optical density at 562 mm of the resulted broths and the results are shown in Table 2 and 3. In Table 2 and 3 the degree of the resistance is represented by the relative values of the growth to the control.

TABLE 2

| Chemical agent | Strains tested | Degree of Resistance Concentration (g/dl) | | | | | |
|---|---|---|---|---|---|---|---|
| | | 0 | 1 | 2 | 4 | 5 | 10 |
| Keto-malonic acid | AJ 3277 | 100 | 59 | | | 8 | 5 |
| | AJ 11595 | " | 100 | | | 100 | 20 |
| | AJ 3278 | " | 44 | | | 5 | 0 |
| | AJ 11598 | " | 100 | | | 95 | 25 |
| Fluoro-malonic acid | AJ 3277 | " | 54 | | | 5 | 0 |
| | AJ 11596 | " | 103 | | | 102 | 60 |
| Monofluoro-acetic acid | AJ 3277 | " | | 45 | 0 | 0 | 60 |
| | AJ 11597 | " | | 110 | 100 | 100 | |
| | AJ 11193 | " | | 53 | 4 | 0 | |
| | AJ 11600 | " | | 110 | 100 | 90 | |
| | AJ 3278 | " | | 47 | 0 | 0 | |
| | AJ 11599 | " | | 110 | 90 | 90 | |

TABLE 3

| Chemical agent | Strains tested | Degree of Resistance Concentration (g/dl) | | | |
|---|---|---|---|---|---|
| | | 0 | 0.1 | 0.5 | 1.0 |
| β-Aspartate hydrazide | AJ 3277 | 100 | 50 | 18 | 8 |
| | AJ 11337 | 100 | 90 | 63 | 27 |
| | AJ 3278 | 100 | 45 | 23 | 8 |
| | AJ 11341 | 100 | 93 | 51 | 19 |
| | AJ 11193 | 100 | 48 | 12 | 7 |
| | AJ 11343 | 100 | 91 | 83 | 13 |
| 2,6-Diamino succinate | AJ 3277 | 100 | 55 | 22 | 10 |
| | AJ 11338 | 100 | 92 | 65 | 25 |
| | AJ 3278 | 100 | 43 | 19 | 5 |
| | AJ 11342 | 100 | 91 | 55 | 23 |
| Hadacidin | AJ 3277 | 100 | 55 | 16 | 9 |
| | AJ 11339 | 100 | 85 | 65 | 23 |
| | AJ 11344 | 100 | 92 | 79 | 17 |
| | AJ 11193 | 100 | 41 | 8 | 4 |

The mutant are cultured aerobically in a conventional culture medium containing carbon sources, nitrogen sources, and inorganic ions, and when required minor nutrients.

As the carbon sources saccharides such as glucose, fructose and sucrose, and molasses and starch hydrolyzed containing those saccharides, organic acids such as acetic acid and propionic acid, and alcohols can be used preferably. Nitrogen source are, for example, ammonia sulfate, gaseous ammonia and urea.

Cultivation is carried out preferably under aerobic condition for 2 to 7 days and the temperature of the culture medium is controlled in the range from 24° to 37° C., preferably adjusting the pH of the medium at 5.0 to 9.0 with organic or inorganic acid or alkali. For this purpose, urea, $CaCO_3$ or gaseous ammonia may also be used.

L-arginine accumulated in the culture broth may be recovered by an entirely conventional recovering method such as using an ion exchanging resine.

The invention will now be illustrated by the following Examples.

EXAMPLE 1

Twenty five ml portions of Culture medium (A) of which the composition is given in Table 4 were put into 500 ml-flasks, and heated at 110° C. for 5 minutes for sterilization. Then each flask was supplemented with 1.0 g $CaCO_3$ separately sterilized.

TABLE 4

| Composition of Culture Medium | | | | | |
|---|---|---|---|---|---|
| Component | | Medium A | B | C | D |
| Glucose | (g/dl) | 10.0 | 3.0 | — | — |
| Ethanol | (g/dl) | — | — | 1.0 | 1.5 |
| Ammonium sulfate | " | 6.0 | 2.0 | 0.5 | — |
| Ammonium acetate | " | — | 0.5 | — | 0.3 |
| Urea | " | — | 0.2 | 0.2 | — |
| $KH_2PO_4$ | " | 0.1 | 0.1 | 0.1 | 0.1 |
| $MgSO_4$ | " | 0.04 | 0.04 | 0.04 | 0.04 |
| $FeSO_4$ | (mg/dl) | 1.0 | 1.0 | 1.0 | 1.0 |
| $MnSO_4$ | " | 1.0 | 1.0 | 1.0 | 1.0 |
| Bitotin | (μg/l) | 50 | 50 | 50 | 50 |
| Thiamine.HCl | " | 20 | 20 | 50 | 200 |
| Soy protein hydrolyzate (7.0%) | (ml/dl) | 1.0 | 2.5 | 2.5 | 1.5 |
| $CaCO_3$ | (g/dl) | 5.0 | — | — | — |
| pH | | 7.0 | 7.5 | 7.5 | 7.5 |

Brevibacterium flavum AJ 11600 and AJ 11343 previously cultured on bovillon agar slants were inoculated into the each bach of culture medium, and cultured with shaking at 31° C. for 72 hours. After 72 hours cultivation, determination of L-arginine accumulated in the resultant culture broth were carried out colorimetrically and the results are shown in Table 5:

TABLE 5

| Strain | L-arginine accumulated |
|---|---|
| AJ 11600 | 3.6 g/dl |
| AJ 11343 | 3.5 g/dl |

One liter of culture broth of AJ 11600 prepared by the same manner as above were collected and centrifuged to remove microbial cells and solid $CaCO_3$. One liter supernatant solution thus obtained was passed through the column of "Amberlite C-50" in the form of $NH_4^+$, thereby L-arginine was adsorbed on the resine, and it was eluted with 2 N ammonia water. The elute was evaporated and the concentrated solution was cooled to a low temperature enough to crystalize L-arginine. After the completion of the crystallization, 23.3 g crystalline L-arginine was separated from the mother liquor.

In a similar manner as above, 22.7 g crystalline L-arginine was obtained from the culture broth of AJ 11343.

EXAMPLE 2

Each of the strains listed in Table 5 previously cultured on a bovillon agar slant was cultured in the same manner as described in Example 1 and the amount of L-arginine accumulated in the cultured broth was determined. The result is given in the table below.

TABLE 5

| Strain | L-arginine accumulated (g/dl) |
|---|---|
| AJ 3277 | 1.80 |
| AJ 11595 | 1.92 |
| AJ 11596 | 1.84 |
| AJ 11597 | 1.90 |
| AJ 11337 | 2.00 |
| AJ 11338 | 1.90 |
| AJ 11339 | 1.85 |
| AJ 3278 | 1.70 |
| AJ 11598 | 1.86 |
| AJ 11599 | 1.91 |
| AJ 11341 | 1.90 |
| AJ 11342 | 1.85 |
| AJ 11193 | 3.30 |
| AJ 11600 | 3.60 |
| AJ 11344 | 3.45 |

EXAMPLE 3

Three hundred ml of Medium (C) shown in Table 4 was placed in 1.0 liter-fermentation vessel and heated at 110° C. for 5 minutes for sterilization. Then it was inoculated with 15 ml seed culture broth of *Brevibacterium flavum* AJ 11599 which had been previously culturing in Medium (D) aerobically at 31° C. with agitation and aeration.

During the cultivation, the pH of the medium was maintained in the range from 7.2 to 8.0 with addition of acetic acid and acetic acid solution.

After 55 hours of the cultivation, 4.24 g/dl L-arginine was accumulated in the culture broth. The volume of acetic acid solution used during the cultivation was 20% to the initial volume of the culture medium. From 300 ml culture broth thus prepared, 9.20 g crystalline L-arginine was obtained in the same manner as described in Example 1.

EXAMPLE 4

*Brevibacterium flavum* AJ 11343 were cultured in Medium (D) shown in Table 4 at 31°0 C. for 18 hours with agitation and aeration to prepare seed culture broth.

Thereafter 300 ml of Medium (C) was placed in 1.0 liter-fermentation vessel, sterilized at 110° C. for 5 minutes, was inoculated with 15 ml of the seed culture broth and held at a temperature of 31° C. with agitation and aeration. During the cultivation, the pH of the medium was maintained at a pH ranging from 7.2 to 7.8 with gaseous ammonia. The concentration of ethanol in the medium was determined by gas-chromatography and small portions of ethanol were fed to the medium when the ethanol concentration became about 0.3%. After 48 hours of the cultivation, 48 g of ethanol was consumed and 2.57 g/dl of L-arginine was found in the culture broth. By the manner shown in Example 1, 4.75 g of L-arginine was recovered.

What is claimed is:

1. A method for the production of L-arginine by fermentation which comprises:
   (1) culturing aerobically in a culture medium a mutant capable of producing L-arginine of the genus Brevibacterium or Corynebacterium, and
   (2) recovering the L-arginine accumulated in the culture medium; said mutant being resistant to Keto-malonic acid, fluoro-malonic acid, monofluoro-acetic acid or aspartate-antagonist, wherein said mutant belongs to the species *Brevibacterium flavum* or *Corynebacterium acetoacidophilum* selected from the class consisting of

| | |
|---|---|
| *Brevibacterium flavum* | NRRL B-12235 |
| *Brevibacterium flavum* | NRRL B-12236 |
| *Brevibacterium flavum* | NRRL B-12237 |
| *Brevibacterium flavum* | NRRL B-12240 |
| *Brevibacterium flavum* | NRRL B-12242 |
| *Brevibacterium flavum* | NRRL B-12243 |
| *Brevibacterium flavum* | NRRL B-12244 |
| *Brevibacterium flavum* | NRRL B-12241 |
| *Brevibacterium flavum* | NRRL B-12247 |
| *Corynebacterium acetoacidophilum* | NRRL B-12238 |
| *Corynebacterium acetoacidophilum* | NRRL B-12239 |
| *Corynebacterium acetoacidophilum* | NRRL B-12245 |
| *Corynebacterium acetoacidophilum* | NRRL B-12246 |

2. The method according to claim 1 where the mutant resistant to keto-malonic acid is *Brevibacterium flavum* NRRL B-12242 or *Brevibacterium flavum* NRRL B-12245.

3. The method according to claim 1 where the mutant resistant to fluoro-malonic acid is *Brevibacterium flavum* NRRL B-12243.

4. The method according to claim 1 where the mutant resistant to monofluoro-acetic acid is *Brevibacterium flavum* NRRL B-12244 or *Brevibacterium flavum* NRRL B-12247, or *Corynebacterium acetoacidophilum* NRRL B-12246.

5. The method according to claim 1 where the mutant resistant to aspartate-antagonist is *Brevibacterium flavum* NRRL B-12235 or *Corynebacterium acetoacidophilum* NRRL B-12238 or *Brevibacterium flavum* NRRL B-12240.

* * * * *